United States Patent
Anderson et al.

(10) Patent No.: US 11,414,403 B2
(45) Date of Patent: Aug. 16, 2022

(54) ANTIBACTERIAL COMPOUND AND USES OF SAME

(71) Applicant: BIOMÉRIEUX, Marcy l'Etoile (FR)

(72) Inventors: Rosaleen Anderson, Marcy l'Etoile (FR); Mark Gray, County Durham (GB); Laszlo Kondacs, Sunderland (GB); Sylvain Orenga, Neuville sur Ain (FR); John Perry, Newcastle Upon Tyne (GB)

(73) Assignee: BIOMERIEUX, Marcy l'Etoile (FR)

( * ) Notice: Subject to any disclaimer, the term of this patent is extended or adjusted under 35 U.S.C. 154(b) by 305 days.

(21) Appl. No.: 16/650,707

(22) PCT Filed: Sep. 24, 2018

(86) PCT No.: PCT/FR2018/052321
§ 371 (c)(1),
(2) Date: Mar. 25, 2020

(87) PCT Pub. No.: WO2019/058074
PCT Pub. Date: Mar. 28, 2019

(65) Prior Publication Data
US 2020/0277281 A1    Sep. 3, 2020

(30) Foreign Application Priority Data
Sep. 25, 2017 (FR) .................................. 1758830

(51) Int. Cl.
*C07D 403/12* (2006.01)
*A01N 43/713* (2006.01)
*C12N 1/20* (2006.01)
*C12Q 1/18* (2006.01)

(52) U.S. Cl.
CPC ......... *C07D 403/12* (2013.01); *A01N 43/713* (2013.01); *C12N 1/20* (2013.01); *C12Q 1/18* (2013.01)

(58) Field of Classification Search
CPC ...... C07D 403/12; A01N 43/713; C12N 1/20; C12Q 1/18
See application file for complete search history.

(56) References Cited

FOREIGN PATENT DOCUMENTS

WO      02/22785 A1    3/2002

OTHER PUBLICATIONS

Andrews, Jennifer M., "Determination of minimum inhibitory concentrations," Journal of Antimicrobial Chemotherapy, 2001, vol. 48, Suppl. S1, pp. 5-16.
Arroyo et al., "Selective action of inhibitors used in different culture media on the competitive microflora of Salmonella," Journal of Applied Bacteriology, 1995, vol. 75, pp. 281-289.
Bavetsias et al., "Design and Synthesis of Cyclopenta[g]quinazoline-Based Antifolates as Inhibitors of Thymidylate Synthase and Potential Antitumor Agents," J. Med. Chem., 2000, vol. 43, pp. 1910-1926.
Nov. 13, 2018 International Search Report issued in International Patent Application No. PCT/FR2018/052321.
Nov. 13, 2018 Written Opinion of the International Searching Authority issued in International Patent Application No. PCT/FR2018/052321.

*Primary Examiner* — Alicia L Otton
(74) *Attorney, Agent, or Firm* — Oliff PLC

(57) ABSTRACT

A new compound exhibiting particularly advantageous antibacterial properties, and having the structural formula:

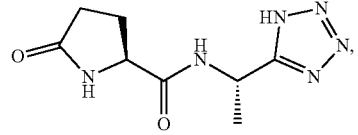

L-pyroglutamyl-L-1-aminoethyltetrazole (or N-(1-(1H-tetrazol-5-yl)ethyl)-5-oxopyrrolidine-2-carboxamide). Also, the use of this compound in microbiological culture methods and media intended for the detection, identification, enrichment, counting and/or isolation of target microorganisms that may be encountered in samples taken for clinical diagnosis or microbiological health control purposes.

8 Claims, 1 Drawing Sheet

ANTIBACTERIAL COMPOUND AND USES OF SAME

BACKGROUND

The invention relates to the field of microbiology, and more particularly the fields of in vitro clinical diagnosis and microbiological health control. The invention relates to a new antibacterial compound and targets the application thereof as a selective agent in microbiological culture methods and media intended for the detection, identification, enrichment, counting and/or isolation of target microorganisms that may be present in a sample to be analyzed and/or to be treated.

Numerous selective agents with antibacterial properties have been developed and used in microbiological culture medium compositions. Each selective agent has a particular, more or less broad, inhibition spectrum, and a more or less marked inhibitory activity depending on the genus and/or the species of the bacteria in question.

Table 1 below lists some of the pathogenic agents most commonly screened for using food, water, clinical and experimental samples. It also sets out the selective agents commonly used in the culture media dedicated to the detection, identification, enrichment, counting and/or isolation of microorganisms, and also some compounds known for their inhibitory effect with regard thereto.

TABLE 1

| Bacterial species | Selective agents | Inhibitor compounds |
|---|---|---|
| Acinetobacter baumannii | Cefsulodin, bile salts, vancomycin | Colistin, gentamicin, polymyxin |
| Burkholderia cepacia | Cetrimide, polymyxin B, vancomycin | Ceftazidime, gentamicin |
| Enterobacter cloacae | Vancomycin, sodium deoxycholate, bile salts | Aztreonam, colistin, polymyxin |
| Escherichia coli | Vancomycin, sodium deoxycholate, bile salts | Aztreonam, alafosfalin, colistin, gentamicin, polymyxin |
| Klebsiella pneumoniae | Vancomycin, sodium deoxycholate, bile salts | Aztreonam, colistin, gentamicin, polymyxin |
| Providencia rettgeri | Vancomycin, sodium deoxycholate, bile salts | Aztreonam |
| Pseudomonas aeruginosa | Vancomycin, sodium deoxycholate, bile salts, cetrimide | Cefsulodin, gentamicin |
| Salmonella typhimurium | Vancomycin, sodium deoxycholate, bile salts, brilliant green | Aztreonam, colistin, gentamicin, polymyxin |
| Serratia marcescens | Vancomycin, sodium deoxycholate, bile salts | Aztreonam, gentamicin |
| Yersinia enterocolitica | Cefsulodin, irgasan, novobiocin | Aztreonam, colistin, gentamicin, polymyxin |
| Salmonella enteritidis | Vancomycin, bile salts, brilliant green | Aztreonam, colistin, gentamicin, polymyxin |
| Bacillus subtilis | Acrylonitrile, polymxyin, streptomycin | Sodium deoxycholate, bile salts, crystal violet, brilliant green, vancomycin |
| Enterococcus faecalis | Sodium azide, colistin, bile salts | Lithium chloride, vancomycin |
| Enterococcus faecium | Sodium azide, colistin, bile salts | Lithium chloride, vancomycin |
| Listeria monocytogenes | Lithium chloride, colistin, polymyxin | Vancomycin, gentamicin |
| Staphylococcus epidermidis | Nalidixic acid, aztreonam, colistin | Vancomycin, gentamicin |
| Staphylococcus aureus MSSA | Sodium chloride, lithium chloride, colistin | Vancomycin, methicillin, cefoxitin, gentamicin |
| Staphylococcus aureus MRSA | Sodium chloride, lithium chloride, methicillin, cefoxitin, colistin | Vancomycin |
| Streptococcus agalactiae | Nalidixic acid, aztrenonam, colistin | Vancomycin, bile salts |

In vitro diagnosis and health control techniques, which aim to demonstrate any microbiological infections or contaminations, are still based on microbiological culture steps which make it possible to amplify, detect, identify, count and/or isolate the microorganisms of interest possibly present in the samples to be analyzed. Because the microorganisms of interest (or target microorganisms) are rarely the only ones present in the samples to be analyzed, and are even quite often in very minor proportions compared with the subsidiary microbial flora (or non-target microorganisms), it is generally necessary to use "selective" culture media, the compositions of which are specifically chosen to optimize the growth and multiplication of the target microorganism(s), while at the same time blocking as much as possible those of the subsidiary microbial flora.

Thus, in addition to having to meet the nutritive requirements of the target microorganisms and to create an environment and conditions that are conducive to these target microorganisms, the composition of the selective culture media also contains selective agents capable of slowing down or blocking the growth (that is to say the growth, development and/or division) of the non-target microorganisms.

SUMMARY

Faced with the very large diversity of microorganisms that surround us, with the diversity of the samples that are subjected to diagnostic or health control tests, and with that of the microbial populations present in these samples, it is advantageous to be able to have the largest possible range of selective agents.

In this regard, the invention provides a new compound exhibiting particularly advantageous antibacterial properties and having the structural formula:

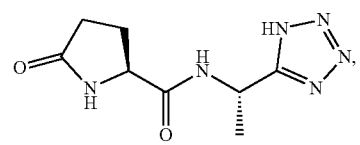 [SMILES: C[C@H](NC(=O)[C@@H]1CCC(=O)N1)c1nnn[nH]1]

L-pyroglutamyl-L-1-aminoethyltetrazole.

The invention also extends to this compound in salt form.

Using the IUPAC nomenclature, this compound can also be denoted: N-(1-(1H-tetrazol-5-yl)ethyl)-5-oxopyrrolidine-2-carboxamide.

DETAILED DESCRIPTION

Figure 1:
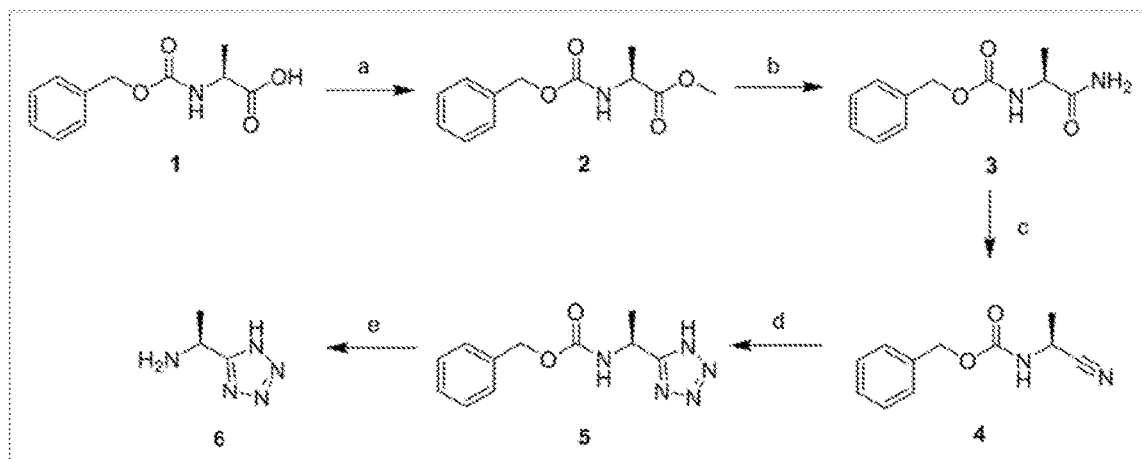
FIGS. 1 to 3 show schematically the progression of a process for synthesizing L-pyroglutamyl-L-1-aminoethyltetrazole.

Before proceeding with the description of the invention, the following definitions are given in order to allow better understanding of said invention and of its interest in the field of microbiology, in particular for microbiological control.

The term "antibacterial compound" is intended to mean a bacteria-inhibiting compound. This inhibitory activity can result in either a bactericidal effect which destroys bacteria, or a bacteriostatic effect, which blocks the growth and/or development of bacteria without however killing them. It should be noted that an antibacterial compound may be bacteriostatic at low dose and bactericidal at a higher dose.

The term "microbiological culture medium" or more simply "culture medium" is intended to mean a preparation used as a support for culturing microorganisms, the composition of which comprises all the elements required for the expression of a metabolism and/or the survival and/or growth of the targeted microorganisms. A culture medium may be liquid, solid or semi-solid. The term "solid medium" or "semi-solid medium" is intended to mean for example a gelled medium. Agar is the conventional gelling agent in microbiology for the preparation of these culture media, but it is possible to use gelatin, agarose or other natural or artificial gelling agents. The "solid" or "semi-solid" nature of the media depends essentially on the content of gelling agent. For the purposes of simplicity, the expression "solid medium" will subsequently be used to denote both a solid medium and a semi-solid medium.

A culture medium is termed "selective" when it comprises at least one selective agent allowing said medium to promote the growth of a target microorganism or of a target group of microorganisms, rather than that of the subsidiary microbial flora (composed of non-target microorganisms). These are essentially antibacterial and/or antifungal compounds, and exhibit a specificity of toxicity (toxicity lower for the target microorganisms than the non-target microorganisms).

The term "selective agent" is intended to mean any compound capable of inhibiting the growth and/or development of a microorganism referred to as "non-target". By way of indication, a selective agent is used, in the selective culture media, at concentrations of between 0.001 and 1024.0 mg/l. It should be noted that the inhibition spectrum of a selective agent can broaden as the concentration increases.

For the purposes of the present invention, the term "in vitro clinical diagnosis" or "microbiological (health) control" is intended to mean the analysis of a sample with the aim of detecting and/or counting microorganisms which are suspected of being/which may be present in said sample.

The term "sample" is intended to mean a small portion or small amount of material that is isolated from its context for the purpose of treatment and/or analysis. A sample may consist of a clinical specimen of human or animal origin (in particular, a blood, stool, urine, mucus membrane, etc., specimen). It may also have an industrial or environmental origin, and may consist of a specimen from air, a specimen from water, a specimen taken on a surface, a part or a manufactured product, a product of food origin (for example a milk product, meat, fish, eggs, fruit/vegetables, a beverage, etc.).

The term "detection" is intended to mean the visualization with a naked eye or with an optical instrument of the presence of the target microorganism(s), or else the demonstration of the presence of the target microorganism(s) by carrying out molecular biology, immunology, spectrometry (in particular mass spectrometry, infrared spectrometry, etc.), chromatography techniques.

The term "identification" is intended to mean a determination of the genus and/or species and/or of the group to which a studied microorganism belongs.

The term "counting" is intended to mean the act of counting/quantifying/evaluating the number of target microorganisms present in a sample tested.

The term "enrichment" is intended to mean the act of increasing, in a microbial population of a sample, the proportion represented by the target microorganism(s) relative to the total microbial population.

By virtue of its particular antibacterial properties, L-pyroglutamyl-L-1-aminoethyltetrazole attracts interest most particularly for the field of microbiological analysis. Beyond the compound in itself, the invention extends to the in vitro use of L-pyroglutamyl-L-1-aminoethyltetrazole as an antibacterial compound and in particular in microbiological culture methods and media intended for the detection, identification, enrichment, counting and/or isolation of microorganisms.

In particular, the invention relates more particularly to an in vitro microbiological culture method, wherein microorganisms that may be present in a sample to be analyzed and/or to be treated are inoculated in or on a microbiological culture medium comprising L-pyroglutamyl-L-1-aminoethyltetrazole, at a non-zero concentration, less than or equal to 1 g/l.

In addition to a marked in vitro antibacterial activity with regard to specific bacterial species, the new compound according to the invention has demonstrated a great modularity of its antibacterial activities of a function of the concentration used.

Thus, in a microbiological culture method according to the invention, the L-pyroglutamyl-L-1-aminoethyltetrazole is advantageously present in the microbiological culture medium at a concentration:

of between 10 and 1000 mg/l, preferably between 16 and 500 mg/l, typically between 30 and 128 mg/l, for inhibiting at least one bacterium chosen from the bacterial species consisting of: *Klebsiella pneumoniae, Serratia marcescens, Yersinia enterocolitica, Bacillus subtilis, Enterococcus faecalis* and *Enterococcus faecium*; or of between 2 and 50 mg/l, preferably between 5 and 15 mg/l, for inhibiting at least one bacterium chosen from the bacterial species consisting of: *Klebsiella pneumoniae, Serratia marcescens, Yersinia enterocolitica, Enterococcus faecalis* and *Enterococcus faecium*; or of between 1 and 10 mg/l, preferably between 3 and 5 mg/l, for inhibiting at least one bacterium chosen from the bacterial species consisting of: *Yersinia enterocolitica, Enterococcus faecalis* and *Enterococcus faecium*; or which is non-zero, less than or equal to 5 mg/l, preferably less than or equal to 3 mg/l, for inhibiting at least one bacterium chosen from the bacterial species consisting of: *Enterococcus faecalis* and *Enterococcus faecium*; said at least one bacterium being capable of being present in the sample to be analyzed and/or to be treated.

Likewise, in a microbiological culture method according to the invention, the L-pyroglutamyl-L-1-aminoethyltetrazole is advantageously present in the microbiological culture medium at a concentration:

- of between 10 and 1000 mg/l, preferably between 16 and 500 mg/l, and typically between 30 and 128 mg/l, with a view to detecting, identifying, counting and/or isolating at least one target microorganism chosen from the bacterial species consisting of: *Acinetobacter baumannii, Burkholderia cepacia, Enterobacter cloacae, Escherichia coli, Providencia rettgeri, Pseudomonas aeruginosa, Salmonella typhimurium, Salmonella enteritidis, Listeria monocytogenes, Staphylococcus epidermidis, Staphylococcus aureus, Streptococcus agalactiae*; or
- of between 2 and 50 mg/l, preferably between 5 and 15 mg/l, with a view to detecting, identifying, counting and/or isolating at least one target microorganism chosen from the bacterial species consisting of: *Acinetobacter baumannii, Burkholderia cepacia, Enterobacter cloacae, Escherichia coli, Providencia rettgeri, Pseudomonas aeruginosa, Salmonella typhimurium, Salmonella enteritidis, Bacillus subtilis, Listeria monocytogenes, Staphylococcus epidermidis, Staphylococcus aureus, Streptococcus agalactiae*; or
- of between 1 and 10 mg/l, preferably between 3 and 5 mg/l, with a view to detecting, identifying, counting and/or isolating at least one target microorganism chosen from the bacterial species consisting of: *Acinetobacter baumannii, Burkholderia cepacia, Enterobacter cloacae, Escherichia coli, Klebsiella pneumoniae, Providencia rettgeri, Pseudomonas aeruginosa, Salmonella typhimurium, Serratia marcescens, Salmonella enteritidis, Bacillus subtilis, Listeria monocytogenes, Staphylococcus epidermidis, Staphylococcus aureus, Streptococcus agalactiae*; or
- which is non-zero, less than or equal to 5 mg/l, preferably less than or equal to 3 mg/l, with a view to detecting, identifying, counting and/or isolating at least one target microorganism chosen from the bacterial species consisting of: *Acinetobacter baumannii, Burkholderia cepacia, Enterobacter cloacae, Escherichia coli, Klebsiella pneumoniae, Providencia rettgeri, Pseudomonas aeruginosa, Salmonella typhimurium, Serratia marcescens, Yersinia enterocolitica, Salmonella enteritidis, Bacillus subtilis, Listeria monocytogenes, Staphylococcus epidermidis, Staphylococcus aureus, Streptococcus agalactiae*; or said at least one target microorganism being capable of being present in the sample to be analyzed and/or to be treated.

Another subject of the invention relates to microbiological culture media comprising, as selective agent, at least L-pyroglutamyl-L-1-aminoethyltetrazole, at a non-zero concentration, of less than or equal to 1 g/l, and preferably a non-zero concentration, less than or equal to 500 mg/l.

According to a first advantageous embodiment, a microbiological culture medium according to the invention comprises, as selective agent, at least L-pyroglutamyl-L-1-aminoethyltetrazole, at a concentration between 10 and 1000 mg/l, preferably between 16 and 500 mg/l, and typically between 30 and 128 mg/l. Such a culture medium is suitable for the detection, identification, counting and/or isolation of at least one target microorganism chosen from the bacterial species consisting of: *Acinetobacter baumannii, Burkholderia cepacia, Enterobacter cloacae, Escherichia coli, Klebsiella pneumoniae, Providencia rettgeri, Pseudomonas aeruginosa, Salmonella typhimurium, Serratia marcescens, Yersinia enterocolitica, Salmonella enteritidis, Bacillus subtilis, Listeria monocytogenes, Staphylococcus epidermidis, Staphylococcus aureus, Streptococcus agalactiae*.

According to a second advantageous embodiment, a microbiological culture medium according to the invention comprises, as selective agent, at least L-pyroglutamyl-L-1-aminoethyltetrazole, at a concentration of between 2 and 50 mg/l, preferably between 5 and 15 mg/l. Such a culture medium is suitable for the detection, identification, counting and/or isolation of at least one target microorganism chosen from the bacterial species consisting of: *Acinetobacter baumannii, Burkholderia cepacia, Enterobacter cloacae, Escherichia coli, Providencia rettgeri, Pseudomonas aeruginosa, Salmonella typhimurium, Salmonella enteritidis, Bacillus subtilis, Listeria monocytogenes, Staphylococcus epidermidis, Staphylococcus aureus, Streptococcus agalactiae*.

According to a third advantageous embodiment, a microbiological culture medium according to the invention comprises, as selective agent, at least L-pyroglutamyl-L-1-aminoethyltetrazole, at a non-zero concentration, less than or equal to 5 mg/l, preferably less than or equal to 3 mg/l. Such a culture medium is suitable for the detection, identification, counting and/or isolation of at least one target microorganism chosen from the bacterial species consisting of: *Acinetobacter baumannii, Burkholderia cepacia, Enterobacter cloacae, Escherichia coli, Klebsiella pneumoniae, Providencia rettgeri, Pseudomonas aeruginosa, Salmonella typhimurium, Serratia marcescens, Salmonella enteritidis, Bacillus subtilis, Listeria monocytogenes, Staphylococcus epidermidis, Staphylococcus aureus, Streptococcus agalactiae*.

Figure 2:
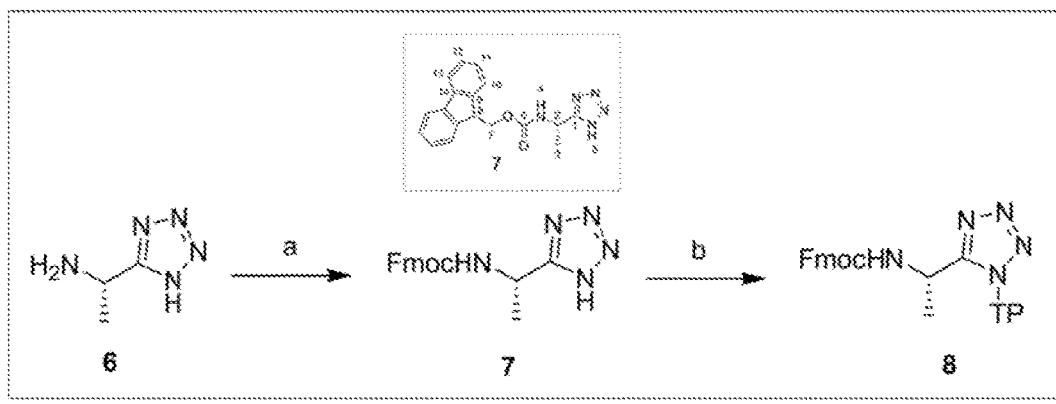
Figure 3:
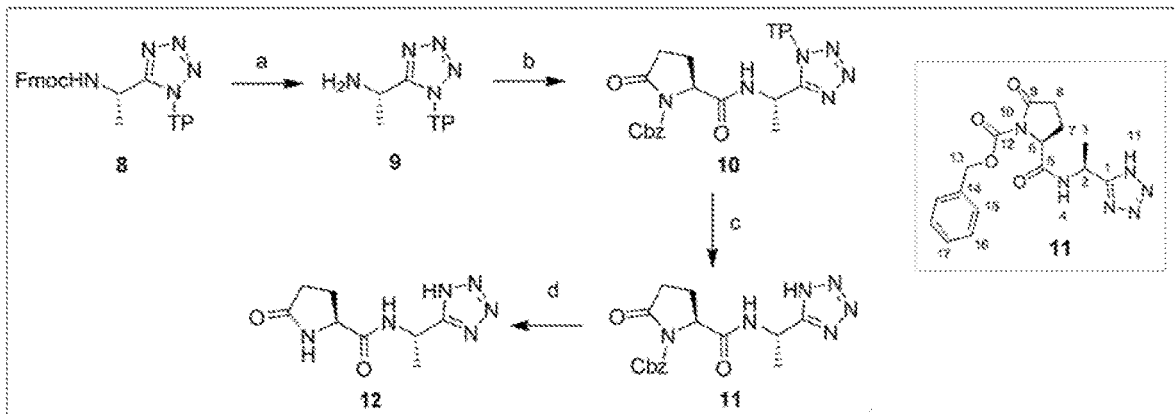

Other objectives, features and advantages of the invention will emerge in the light of the description which follows and the examples developed below. FIGS. 1 to 3, referenced in this description, and these examples show schematically the progression of a process for synthesizing L-pyroglutamyl-L-1-aminoethyltetrazole.

The objective of these examples is to facilitate understanding of the invention, the implementation thereof and the use thereof. These examples are given by way of explanation and could not limit the scope of the invention.

EXAMPLES

Example 1: Synthesis of the Compounds of Interest and Analytical Data 1.1. General Considerations The synthesis of the compounds of interest for the implementation of the present invention is shown below, with reference to FIGS. 1 to 3.

The monitoring of these syntheses and the characterization of the final and intermediate products were carried out by various analysis methods and in particular by magnetic resonance spectroscopy, infrared spectroscopy, mass spectroscopy, melting point determination, and thin layer chromatography.

The NMR spectra are obtained using a Bruker Ultrashield 300 spectrometer (at 300 MHz for the $^1$H spectra and at 75 MHz for the $^{13}$C spectra), and a Bruker Avance III Ultrashield spectrometer (at 500 MHz for the $^1$H spectra and at 125 MHz for the $^{13}C$ spectra). The melting points $M_p$ are recorded by means a Reichert-Kofler microscope with a heating stage (the values disclosed are uncorrected). The IR spectra are recorded over a range of 4000-600 cm$^{-1}$, using a Perkin Elmer Spectrum BX FT-IR spectrophotometer. The low-resolution mass spectra were recorded on a Bruker Esquire 3000 Plus analyzer using the electro-spray source, either in positive ion mode or in negative ion mode. The elemental analyses are carried out using an Exeter Analytical CE-440 Elemental. The thin layer chromatographies were carried out on Merck 60F254 silica gels. Silica 60 (35-70 μm) gels from Fisons are used to carry out the flash chromatography; these samples are pre-absorbed on the silica 60 (35-70 μm). Hydrogenation reactions are carried out with a mini reactor distributed by the company Parr, the 4560 Mini Bench Top Reactor.

Only some of the data collected are presented below and relate only to compounds judged to be important for the understanding and the definition of the present invention.

1.2. L-1-aminoethyltetrazole (6)

Synthesis:

The synthesis of L-1-aminoethyltetrazole (6) is carried out according to the synthesis method described by Bavetsias et al., 2000 (J. Med. Chem. 2000, 43, 1910) and into which minor modifications have been introduced. The corresponding reaction scheme is presented in FIG. 1.

In step (a), the Cbz-L-alanine (1) is methylated with methyl iodide in the presence of $Cs_2CO_3$ in DMF.

To do this, cesium carbonate (8.03 g; 25.0 mmol) is added to a solution of Cbz-L-alanine (1) (10.0 g; 45.0 mmol) in anhydrous DMF (70 ml). The whole mixture is stirred for 30 minutes at ambient temperature, then stirred again overnight after the dropwise addition of methyl iodide (2.94 ml, 47.0 mmol). Once the reaction is complete, ethyl acetate (50 ml) is added and the mixture is washed with water (3×50 ml); the combined aqueous phase is then extracted with ethyl acetate (50 ml). The combined organic phase is washed with a 10% $K_2CO_3$ solution (2×30 ml), with brine (30 ml), and then dried over $MgSO_4$. The solvent is eliminated under reduced pressure to give a methyl ester, methyl (2S)-2-{[(benzyloxy)carbonyl]amino}propanoate or Cbz-L-alanine methyl ester (2), which is in the form of a white solid (10.6 g; 99%).

The Cbz-L-alanine methyl ester (2) is then converted, in step (b), into an amide, benzyl-N-[(1S)-1-carbamoylethyl]carbamate (3). To this effect, this methyl ester (2) (10.00 g; 420 mmol) is dissolved and stirred in a solution of 7 M aqueous ammonia and of methanol (60 ml), at 50° C. and in a sealed tube, overnight. Once the reaction is complete, the mixture is evaporated off under reduced pressure to give benzyl-N-[(1S)-1-carbamoylethyl]carbamate or Cbz-L-alanine amide (3), which is in the form of a white powder (9.40 g; 99%).

Step (c) makes it possible to convert the Cbz-L-alanine amide (3) into benzyl-N-[(1S)-1-cyanoethyl]carbamate or Cbz-L-alanyl nitrile (4). To do this, Cbz-L-alanine amide (3) (9.70 g; 44.0 mmol) is dissolved in DCM (21 ml), and pyridine (33 ml) is added thereto. After cooling to 0° C., tosyl chloride (16.72 g; 88.0 mmol) is added, and the whole mixture is stirred for 30 minutes at 0° C. then overnight at ambient temperature. Once the reaction is complete, the system is cooled to 0° C., and blocked with water (160 ml) and ethyl acetate (160 ml). After separation, the aqueous layer is extracted with ethyl acetate (4×80 ml) and the combined organic phase is washed with 1.2 M HCl (3×80 ml) and with saturated $NaHCO_3$ (80 ml), then with brine (80 ml). The total solution is then dried over $MgSO_4$ and evaporated under reduced pressure. The crude product is washed with heptane to give the compound (4). This compound (4) is in the form of white crystals (8.48 g; 94%).

Step (d) makes it possible to convert the Cbz-L-alanyl nitrite (4) into benzyl-N-[(1S)-1-(1H-1,2,3,4-tetrazol-5-yl)ethyl]carbamate or Cbz-L-1-aminoethyltetrazole (5), by means of a dipolar cycloaddition reaction with $NaN_3$. To do this, $NH_4Cl$ (2.03 g; 38 mmol) and $NaN_3$ (2.62 g; 38 mmol) are suspended in anhydrous DMF (60 ml) inside a two-necked round-bottomed flask, equipped with a reflux condenser and a drying tube. The Cbz-L-alanyl nitrile (4) is added thereto (7.80 g, 38 mmol). The mixture is stirred and heated at 90° C. for 1 hour. Another portion of $NH_4Cl$ (1.04 g; 19 mmol) and $NaN_3$ (1.31 g; 19 mmol) is added to the cooled mixture and the resulting mixture is heated at 90° C. overnight. Once the reaction is complete, the mixture is filtered and the residue is washed with ethyl acetate. The filtrate is evaporated under reduced pressure. Water (180 ml) is added to the residue and the whole mixture is acidified to a pH of 1 with an aqueous 2.5 M HCl solution. The precipitate is separated by filtration and washed with water to give the Cbz-L-1-aminoethyltetrazole (5), in the form of a white solid (7.55 g; 80%).

In step (e), the L-1-aminoethyltetrazole (6) is finally obtained by eliminating the Cbz protective group. This deprotection is obtained by means of a palladium-catalyzed hydrogenation reaction. To do this, a solution of Cbz-L-1-aminoethyltetrazole (5) (0.75 g; 3.0 mmol) in methanol is prepared, 1 meq of palladium on active carbon (5% Pd) is added thereto. The mixture is stirred at ambient temperature under 2 bar of hydrogen pressure overnight in an autoclave. Once the reaction is complete, the mixture is filtered through celite. After filtration, the solid residue is washed with ethanol and the filtrate is evaporated over reduced pressure. The L-1-aminoethyltetrazole (6) obtained is in the form of a white solid (0.33 g; 97%).

The overall yield of this L-1-aminoethyltetrazole (6) synthesis is about 71%.

Characterization:

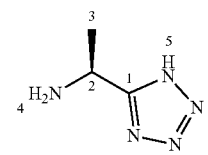

(1S)-1-(1H-1,2,3,4-tetrazol-5-yl)ethan-1-amine $M_p$=230° C.

$^1H$ NMR (300 MHz, DMSO-d$_6$) $\delta_H$ 4.55 (1H, quart, J=6.6 Hz, 2-H), 1.54 (3H, d, J=6.9 Hz, 3-H); $^{13}C$ NMR (75.5 MHz, DMSO-d$_6$) $\delta_C$ 160.4 (1-C), 44.1 (2-C), 19.8 (3-C); $\nu_{max}$/cm$^{-1}$ 3388 (N—H), 2916, 2719, 2634, 2522 (tetrazole); MS(ESI) m/z 114.1 (M+H)$^+$.

1.3. L-pyroglutamyl-L-1-aminoethyltetrazole

The L-pyroglutamyl-L-1-aminoethyltetrazole (12), or (S)-N-((S)-1-(1H-tetrazol-5-yl)ethyl)-5-oxopyrrolidine-2-carboxamide, can be prepared according to a solid-phase synthesis approach, in which the starting point is an L-1-aminoethyltetrazole (6) attached to a resin of 2-chlorotrityl chloride (TP) and the amine function of which is protected by an Fmoc protective group.

a) Preparation of Fmoc-L-1-aminoethyltetrazole Attached to a Resin (8)

The approach used is that described by Chan and White ("Fmoc solid phase peptide synthesis☐, 2000). The corresponding reaction scheme is presented in FIG. 2.

The amine function of the L-1-aminoethyltetrazole (6) is protected with an Fmoc. (fluorenylmethoxycarbonyl) protective group, using Fmoc chloride in the presence of $Na_2CO_3$, in a 2-phase heterogeneous reaction. Subsequently, the Fmoc-L-1-aminoethyltetrazole (7) is attached to the 2-chlorotrityl chloride resin.

b) Synthesis of L-pyroglutamyl-L-1-aminoethyltetrazole (12)

The corresponding reaction scheme is presented in FIG. 3.

In step (a), the Fmoc protective group of the Fmoc-L-1-aminoethyltetrazole compound (8), attached to the resin, is eliminated with 25% piperidine solution in DMF. In step (b) the free amine function is coupled with Cbz-Pyr-OH using HBTU as coupling agent and DIPEA as non-nucleophilic base in DMF. In step (c), the Cbz-L-pyroglutamyl-L-1-aminoethyltetrazole (10) attached to the resin is cleaved from the resin by a TFA/DCM/TIS mixture in a 5:95:1 equivalent ratio. In step (d), the Cbz-L-pyroglutamyl-L-1-aminoethyltetrazole (11) is freed of its Cbz protective group by means of a palladium-catalyzed hydrogenation reaction.
Characterization:

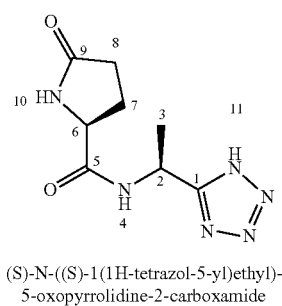

(S)-N-((S)-1(1H-tetrazol-5-yl)ethyl)-5-oxopyrrolidine-2-carboxamide

Molar mass: 224.22 g/mol
$M_p$: 160° C. (decomposed);
$^1H$ NMR (300 MHz, $D_2O$) $\delta_H$ 5.35 (1H, quart, J=7.2 Hz, 2-H), 4.34 (1H, dd, J=4.8 Hz, J=8.4 Hz, 6-H), 2.52 (1H, m, 7-$H_a$), 2.40 (2H, m, 8-H) 2.04 (1H, m, 7-$H_b$), 1.61 (3H, d, J=6.9 Hz, 3-H); $^{13}C$ NMR (75.5 MHz, $D_2O$) $\delta_C$ 182.3 (9-C), 174.6 (5-C), 159.0 (1-C), 56.9 (6-C), 41.0 (2-C), 29.3 (8-C), 25.0 (7-C), 18.1 (3-C); $v_{max}/cm^{-1}$ 3262 (N—H), 1649 (C=O), 1547 (N—H); MS(ESI) m/z 225.1 (M+H)$^+$ Example 2: Evaluation of the Antibacterial Activity of L-pyroglutamyl-L-1-aminoethyltetrazole (12)

The minimum inhibitory concentrations (MICs) of L-pyroglutamyl-L-1-aminoethyltetrazole (12) for 13 Gram-negative strains of bacteria and 8 Gram-positive strains of bacteria were determined using an agar dilution method described by Andrews J M. 2001 ("Determination of minimum inhibitory concentrations☐; J. Antimicrob. Chemother. (2001) 48 Suppl. 1:5-16). Said method required the use of a defined antagonist-free medium (without peptone), prepared in the way previously described with the inclusion of 2% saponin-lysed horse blood, 25.0 µg/ml of NAD and 25.0 µg/ml of hemin (Atherton et al., 1979; "Phosphonopeptides as antibacterial agents: rationale, chemistry, and structure-activity relationships☐; Antimicrob. Agents Chemother. (1979) 15:677-683). The L-pyroglutamyl-L-1-aminoethyltetrazole (12) was dissolved in sterile deionized water and incorporated into the agar medium in a concentration range of 1 to 128 µg/ml. All the isolates were prepared at a density equivalent to 0.5 CFU in sterile deionized water using a densitometer (approximately 1.5×10$^8$ CFU/ml), then diluted to 1 in 15. A 1 µl aliquot of each diluted suspension was then placed on dishes with a multispot inoculator to give the recommended final inoculation of 10 000 CFU/spot (Andrews, 2001. "Determination of minimum inhibitory concentrations"; J. Antimicrob. Chemother. 48 Suppl 1:5-16). All the dishes (including the antimicrobial-free controls) were incubated for 22 hours at 37° C. All the tests were carried out on at least two independent replicates in order to examine the reproducibility.

The bacterial isolates tested all come from international collections, the American Type Culture Collection (ATCC) and the National Collection of Type Cultures (NCTC).

The MIC measurement results obtained are presented in table 2 below.

TABLE 2

| | Growth at various concentrations (mg/l) | | | | | | | | | MIC |
|---|---|---|---|---|---|---|---|---|---|---|
| | 0 | 1 | 2 | 4 | 8 | 16 | 32 | 64 | 128 | (mg/l) |
| *Acinetobacter baumannii* ATCC 19606 | + | + | + | + | + | + | + | + | + | >128 |
| *Burkholderia cepacia* ATCC 25416 | + | + | + | + | + | + | + | + | + | >128 |
| *Enterobacter cloacae* NCTC 11936 | + | + | + | + | + | + | + | + | + | >128 |
| *Escherichia coli* NCTC 10418 | + | + | + | + | + | + | + | + | + | >128 |
| *Escherichia coli* NCTC 12241 | + | + | + | + | + | + | + | + | + | >128 |
| *Klebsiella pneumoniae* NCTC 9528 | + | + | + | Tr. | − | − | − | − | − | 8 |
| *Providencia rettgeri* NCTC 7475 | + | + | + | + | + | + | + | + | + | >128 |
| *Pseudomonas aeruginosa* NCTC 10662 | + | + | + | + | + | + | + | + | + | >128 |
| *Salmonella typhimurium* NCTC 74 | + | + | + | + | + | + | + | + | + | >128 |
| *Serratia marcescens* NCTC 10211 | + | + | + | + | − | − | − | − | − | 8 |
| *Yersinia enterocolitica* NCTC 11176 | + | + | Tr. | − | − | − | − | − | − | 4 |
| *Salmonella enteritidis* NCTC 74 | + | + | + | + | + | + | + | + | + | >128 |
| *Salmonella enteritidis* NCTC 6676 | + | + | + | + | + | + | + | + | + | >128 |
| *Bacillus subtilis* NCTC 9372 | + | + | + | + | + | +/− | +/− | − | − | 64 |
| *Enterococcus faecalis* NCTC 775 | +/− | +/− | − | − | − | − | − | − | − | 2 |
| *Enterococcus faecium* NCTC 7171 | +/− | +/− | − | − | − | − | − | − | − | 2 |

TABLE 2-continued

| | Growth at various concentrations (mg/l) | | | | | | | | | MIC |
|---|---|---|---|---|---|---|---|---|---|---|
| | 0 | 1 | 2 | 4 | 8 | 16 | 32 | 64 | 128 | (mg/l) |
| Listeria monocytogenes NCTC 11994 | + | + | + | + | + | + | + | + | + | >128 |
| Staphylococcus epidermidis NCTC 11047 | + | + | + | + | + | + | + | + | + | >128 |
| Staphylococcus aureus (MSSA) NCTC 6571 | + | + | + | + | + | + | + | + | + | >128 |
| Staphylococcus aureus (MRSA) NCTC 11939 | + | + | + | + | + | + | + | + | + | >128 |
| Streptococcus agalactiae NCTC 8181 | + | + | + | + | + | + | + | + | + | >128 |

According to the data presented, the L-pyroglutamyl-L-1-aminoethyltetrazole (12) exhibits an antibacterial activity that is more or less pronounced depending on the bacterial species in question. It is highly inhibitory with respect to the strains of certain species of bacteria, both gram-negative and gram-positive, in particular *Klebsiella pneumoniae, Serratia marcescens, Yersinia enterocolitica, Bacillus subtilis, Enterococcus faecalis* and *Enterococcus faecium*. At very low concentrations, of about 2 mg/l, the L-pyroglutamyl-L-1-aminoethyltetrazole (12) exhibits an excellent inhibition specificity for enterococci.

The very significant differences in inhibitory concentration observed between the various species of bacteria make L-pyroglutamyl-L-1-aminoethyltetrazole (12) a selective agent that is particularly suitable for microbiological culture media allowing the selective search for, isolation and/or enrichment of certain species of bacteria, and more particularly of bacteria belonging to the species *Acinetobacter baumannii, Burkholderia cepacia, Enterobacter cloacae, Escherichia coli, Providencia rettgeri, Pseudomonas aeruginosa, Salmonella typhimurium, Salmonella enteritidis, Listeria monocytogenes, Staphylococcus epidermidis, Staphylococcus aureus* and *Streptococcus agalactiae*.

The invention claimed is:

1. L-pyroglutamyl-L-1-aminoethyltetrazole having the structural formula:

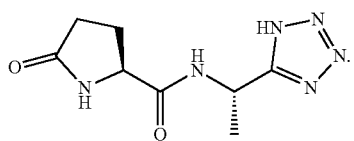 [SMILES: C[C@H](NC(=O)[C@@H]1CCC(=O)N1)c1nnn[nH]1]

12

2. An in vitro microbiological culture method, wherein microorganisms that may be present in a sample to be analyzed and/or to be treated are inoculated in or on a microbiological culture medium comprising L-pyroglutamyl-L-1-aminoethyltetrazole (12) as claimed in claim 1, at a non-zero concentration, less than or equal to 1 g/l.

3. The culture method as claimed in claim 2, wherein the L-pyroglutamyl-L-1-aminoethyltetrazole is present in the microbiological culture medium at a concentration:
of between 10 and 1, 1000 mg/l for inhibiting at least one bacterium chosen from the bacterial species consisting of: *Klebsiella pneumoniae, Serratia marcescens, Yersinia enterocolitica, Bacillus subtilis, Enterococcus faecalis* and *Enterococcus faecium*; or of between 2 and 50 mg/l for inhibiting at least one bacterium chosen from the bacterial species consisting of: *Klebsiella pneumoniae, Serratia marcescens, Yersinia enterocolitica, Enterococcus faecalis* and *Enterococcus faecium*; or
of between 1 and 10 mg/l for inhibiting at least one bacterium chosen from the bacterial species consisting of: *Yersinia enterocolitica, Enterococcus faecalis* and *Enterococcus faecium*; or
which is non-zero, less than or equal to 5 mg/l for inhibiting at least one bacterium chosen from the bacterial species consisting of: *Enterococcus faecalis* and *Enterococcus faecium*;
the at least one bacterium being capable of being present in the sample to be analyzed and/or to be treated.

4. The culture method as claimed in claim 2, wherein the L-pyroglutamyl-L-1-aminoethyltetrazole is present in the microbiological culture medium at a concentration:
of between 10 and 1,1000 mg/l with a view to detecting, identifying, counting and/or isolating at least one target microorganism chosen from the bacterial species consisting of: *Acinetobacter baumannii, Burkholderia cepacia, Enterobacter cloacae, Escherichia coli, Providencia rettgeri, Pseudomonas aeruginosa, Salmonella typhimurium, Salmonella enteritidis, Listeria monocytogenes, Staphylococcus epidermidis, Staphylococcus aureus, Streptococcus agalactiae*; or
of between 2 and 50 mg/l with a view to detecting, identifying, counting and/or isolating at least one target microorganism chosen from the bacterial species consisting of: *Acinetobacter baumannii, Burkholderia cepacia, Enterobacter cloacae, Escherichia coli, Providencia rettgeri, Pseudomonas aeruginosa, Salmonella typhimurium, Salmonella enteritidis, Bacillus subtilis, Listeria monocytogenes, Staphylococcus epidermidis, Staphylococcus aureus, Streptococcus agalactiae*; or
of between 1 and 10 mg/l with a view to detecting, identifying, counting and/or isolating at least one target microorganism chosen from the bacterial species consisting of: *Acinetobacter baumannii, Burkholderia cepacia, Enterobacter cloacae, Escherichia coli, Klebsiella pneumoniae, Providencia rettgeri, Pseudomonas aeruginosa, Salmonella typhimurium, Serratia marcescens, Salmonella enteritidis, Bacillus subtilis, Listeria monocytogenes, Staphylococcus epidermidis, Staphylococcus aureus, Streptococcus agalactiae*; or
which is non-zero, less than or equal to 5 mg/l with a view to detecting, identifying, counting and/or isolating at least one target microorganism chosen from the bacterial species consisting of: *Acinetobacter baumannii, Burkholderia cepacia, Enterobacter cloacae, Escherichia coli, Klebsiella pneumoniae, Providencia rettgeri, Pseudomonas aeruginosa, Salmonella typhimurium, Serratia marcescens, Yersinia enterocolitica, Salmonella enteritidis, Bacillus subtilis, Listeria monocytogenes, Staphylococcus epidermidis, Staphylococcus aureus, Streptococcus agalactiae*; or
the at least one target microorganism being capable of being present in the sample to be analyzed and/or to be treated.

5. A microbiological culture medium comprising, as selective agent, at least L-pyroglutamyl-L-1-aminoethyltetrazole (12) as claimed in claim 1, at a non-zero concentration, less than or equal to 1 g/l.

6. The microbiological culture medium as claimed in claim 5, for the detection, identification, counting and/or isolation of at least one target microorganism chosen from the bacterial species consisting of: *Acinetobacter baumannii, Burkholderia cepacia, Enterobacter cloacae, Escherichia coli, Klebsiella pneumoniae, Providencia rettgeri, Pseudomonas aeruginosa, Salmonella typhimurium, Serratia marcescens, Yersinia enterocolitica, Salmonella enteritidis, Bacillus subtilis, Listeria monocytogenes, Staphylococcus epidermidis, Staphylococcus aureus, Streptococcus agalactiae;* wherein the L-pyroglutamyl-L-1-aminoethyltetrazole is present at a concentration of between 10 and 1000 mg/l.

7. The microbiological culture medium as claimed in claim 5, for the detection, identification, counting and/or isolation of at least one target microorganism chosen from the bacterial species consisting of: *Acinetobacter baumannii, Burkholderia cepacia, Enterobacter cloacae, Escherichia coli, Providencia rettgeri, Pseudomonas aeruginosa, Salmonella typhimurium, Salmonella enteritidis, Bacillus subtilis, Listeria monocytogenes, Staphylococcus epidermidis, Staphylococcus aureus, Streptococcus agalactiae;* wherein the L-pyroglutamyl-L-1-aminoethyltetrazole is present at a concentration of between 2 and mg/l.

8. The microbiological culture medium as claimed in claim 5, for the detection, identification, counting and/or isolation of at least one target microorganism chosen for the bacterial species consisting of: *Acinetobacter baumannii, Burkholderia cepacia, Enterobacter cloacae, Escherichia coli, Klebsiella pneumoniae, Providencia rettgeri, Pseudomonas aeruginosa, Salmonella typhimurium, Serratia marcescens, Salmonella enteritidis, Bacillus subtilis, Listeria monocytogenes, Staphylococcus epidermidis, Staphylococcus aureus, Streptococcus agalactiae;* wherein the L-pyroglutamyl-L-1-aminoethyltetrazole is present at a non-zero concentration, less than or equal to 5 mg/l.

* * * * *